United States Patent
Lanzendörfer et al.

(10) Patent No.: US 6,620,420 B2
(45) Date of Patent: Sep. 16, 2003

(54) GEL CREAMS IN THE FORM OF O/W EMULSIONS CONTAINING ONE OR MORE AMMONIUM ACRYLOYLDIMETHYLTAURATE/ VINYLPYRROLIDONE COPOLYMERS

(75) Inventors: Ghita Lanzendörfer, Hamburg (DE); Jens Nielsen, Henstedt-Ulzburg (DE); Birgit Hargens, Hamburg (DE); Rainer Kröpke, Schenefeld (DE); Heidi Riedel, Hamburg (DE); Stephanie von Thaden, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 10/025,062

(22) Filed: Dec. 19, 2001

(65) Prior Publication Data

US 2002/0155076 A1 Oct. 24, 2002

(30) Foreign Application Priority Data

Dec. 23, 2000 (DE) .......................................... 100 65 047

(51) Int. Cl.[7] ............... A61K 6/00; A61K 7/00

(52) U.S. Cl. ..................... 424/401; 424/400; 514/772.5
(58) Field of Search ....................... 424/63, 401, 78.03; 514/937, 944, 772.5

(56) References Cited

U.S. PATENT DOCUMENTS 6,419,938 B1 * 7/2002 Riedel et al. ............... 424/401

* cited by examiner

Primary Examiner—Thurman K. Page
Assistant Examiner—S. Howard
(74) Attorney, Agent, or Firm—Norris McLaughlin & Marcus

(57) ABSTRACT

Cosmetic or dermatological gel creams of the oil-in-water type, comprising (i) up to 90% by weight of a water phase,
(ii) up to 20% by weight of a lipid phase, based on the total weight of the preparations,
(iii) up to 5% by weight of one or more emulsifiers,
(iv) also comprising up to 5% by weight of one or more ammonium acryloyldimethyltaurates/vinylpyrrolidone copolymers.

9 Claims, No Drawings

GEL CREAMS IN THE FORM OF O/W EMULSIONS CONTAINING ONE OR MORE AMMONIUM ACRYLOYLDIMETHYLTAURATE/ VINYLPYRROLIDONE COPOLYMERS

The present invention relates to cosmetic and dermatological preparations, in particular those of the oil-in-water type, to processes for their preparation, and to their use for cosmetic and medicinal purposes.

The human skin is man's largest organ and performs a number of vital functions. Having an average area of about 2 m² in adults, it has a prominent role as a protective and sensory organ. The purpose of this organ is to transmit and avert mechanical, thermal, actinic, chemical and biological stimuli. In addition, it has an important role as a regulatory and target organ in human metabolism.

The main aim of skin care in the cosmetics sense is to strengthen or restore the skin's natural function as a barrier against environmental influences (e.g. dirt, chemicals, microorganisms) and against the loss of endogenous substances (e.g. water, natural fats, electrolytes), and also to assist its horny layer in its natural regeneration ability in cases of existing damage.

If the barrier properties of the skin are impaired, increased resorption of toxic or allergenic substances or attack by microorganisms may result, leading to toxic or allergic skin reactions.

Another aim of skin care is to compensate for the loss by the skin of sebum and water caused by daily washing. This is particularly important if the natural regeneration ability is inadequate. Furthermore, skin care products should protect against environmental influences, in particular against sun and wind, and delay skin aging.

Medicinal topical compositions usually comprise one or more medicaments in an effective concentration. For the sake of simplicity, in order to clearly distinguish between cosmetic and medicinal use and corresponding products, reference is made to the legal provisions in the Federal Republic of Germany (e.g. Cosmetics Directive, Foods and Drugs Act).

Emulsions are generally understood as meaning heterogeneous systems which consist of two liquids, which are usually referred to as phases, which are immiscible or miscible with one another only to a limited extent. In an emulsion, one of the two liquids is dispersed in the form of very fine droplets in the other liquid.

If the two liquids are water and oil and oil droplets are very finely dispersed in water, this is an oil-in-water emulsion (O/W emulsion, e.g. milk). The basic character of an O/W emulsion is determined by the water. In the case of a water-in-oil emulsion (W/O emulsion, e.g. butter), the principle is reversed, the basic character being determined here by the oil.

Gel creams are particularly light-weight products with a low emulsifier and lipid content. They are characterized by the fact that they can be distributed readily on the skin and impart a feeling of freshness. Following product application, no or only very little residue should remain on the skin. Gel creams generally comprise a relatively high proportion of hydrophilic thickeners (e.g. carbopols, xanthan gum, hydroxyethylcellulose. Since the thickener or the thickener system is in the external phase, it has a significant influence on the sensory properties of the product. Common thickener systems either cannot be readily distributed, do not give a feeling of freshness or leave behind too sticky a residue on the skin.

The aim was to remedy these shortcomings.

Surprisingly, these objects are achieved by cosmetic or dermatological gel creams of the oil-in-water type, comprising (i) up to 90% by weight of a water phase,
(ii) up to 20% by weight of a lipid phase, based on the total weight of the preparations,
(iii) up to 5% by weight of one or more emulsifiers,
(iv) also comprising up to 5% by weight of one or more ammonium acryloyldimethyltaurates/vinylpyrrolidone copolymers.

According to the invention, the ammonium acryloyldimethyltaurates/vinylpyrrolidone copolymer(s) have the empirical formula $[C_7H_{16}N_2SO_4]_n\ [C_6H_9NO]_m$, corresponding to a statistical structure as follows

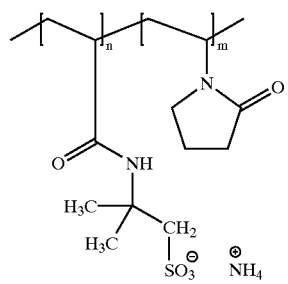

Preferred species for the purposes of the present invention are filed in Chemical Abstracts under the registry numbers 58374-69-9, 13162-05-5 and 88-12-0 and are obtainable under the trade name Aristoflex® AVC from Clariant GmbH.

It had therefore not been foreseen by the person skilled in the art that the preparations according to the invention
would have better effectiveness as moisture-donating preparations,
would be easier to formulate,
would better promote skin smoothing,
would be characterized by better care action,
would better serve as vehicles for cosmetic and medicinal-dermatological active ingredients
would have better sensory properties, such as, for example, the ability to be distributed on the skin or the ability to be absorbed into the skin,
would have higher stability against decomposition in oil and water phases and
would be characterized by better biocompatibility than the preparations of the prior art.

The preparations according to the invention thus represent an enrichment of the prior art.

The lipid content of the preparations obtainable according to the invention can advantageously be varied from 0.5% by weight to 20% by weight, preferably from 5 to 10% by weight, where the results achieved are equally favorable. In the case of freedom from lipid, no emulsion is present, but rather a system which should most appropriately be referred to as an emulsifier gel.

Preparations according to the invention preferably comprise up to 7.5% by weight of a lipid phase, in which case they are O/W emulsions. Preparations according to the invention particularly advantageously comprise up to 6% by weight of a lipid phase. Preparations according to the invention particularly preferably comprise 2 to 4% by weight of a lipid phase, in particular approximately 3% by weight, in each case based on the total weight of the preparations.

The lipid phase of the cosmetic or dermatological emulsions according to the invention can advantageously be chosen from the following group of substances:

mineral oils, mineral waxes oils, such as triglycerides of capric or of caprylic acid, and also natural oils such as, for example, castor oil;

fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;

alkyl benzoates;

silicone oils, such as dimethylpolysiloxanes, diethylpolysiloxanes, diphenylpolysiloxanes and mixed forms thereof.

The oil phase of the emulsions of the present invention is advantageously chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semi-synthetic and natural mixtures of such esters, e.g. jojoba oil.

In addition, the oil phase can advantageously be chosen from the group of branched and unbranched hydrocarbons and hydrocarbon waxes, of silicone oils, of dialkyl ethers, the group of saturated or unsaturated, branched or unbranched alcohols, and the fatty acid triglycerides, namely the triglycerol esters of saturated and/or unsaturated, branched and/or unbranched alkanecarboxylic acids having a chain length of from 8 to 24, in particular 12–18 carbon atoms. The fatty acid triglycerides can, for example, advantageously be chosen from the group of synthetic, semisynthetic and natural oils, e.g. olive oil, sunflower oil, soybean oil, groundnut oil, rapeseed oil, almond oil, palm oil, coconut oil, palm kernel oil and the like.

Any mixtures of such oil and wax components can also be used advantageously for the purposes of the present invention. It may also in some instances be advantageous to use waxes, for example cetyl palmitate, as the sole lipid component of the oil phase.

The oil phase is advantageously chosen from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric triglyceride, dicaprylyl ether.

Particularly advantageous mixtures are those of $C_{12-15}$-alkyl benzoate and 2-ethylhexyl isostearate, mixtures of $C_{12-15}$-alkyl benzoate and isotridecyl isononanoate, and mixtures of $C_{12-15}$-alkyl benzoate, 2-ethylhexyl isostearate and isotridecyl isononanoate.

Of the hydrocarbons, paraffin oil, squalane and squalene are to be used advantageously for the purposes of the present invention.

The oil phase can advantageously also have a content of cyclic or linear silicone oils, or consist entirely of such oils, although it is preferable to use an additional content of other oil phase components apart from the silicone oil or the silicone oils. Such silicones or silicone oils may be in the form of monomers, which are generally characterized by structural elements, as follows:

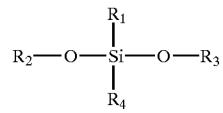

Linear silicones having two or more siloxyl units which are to be used advantageously according to the invention are generally characterized by structural elements, as follows:

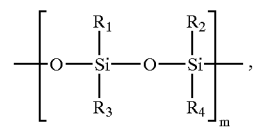

where the silicon atoms can be substituted by identical or different alkyl radicals and/or aryl radicals, which are shown here in general terms by the radicals $R_1$–$R_4$ (that is to say the number of different radicals is not necessarily limited to 4). m can assume values from 2–200 000.

Cyclic silicones to be used advantageously according to the invention are generally characterized by structural elements, as follows

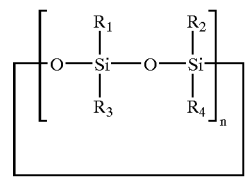

where the silicon atoms can be substituted by identical or different alkyl radicals and/or aryl radicals, which are shown here in general terms by the radicals $R_1$–$R_4$ (that is to say the number of different radicals is not necessarily limited to 4). n can assume values from 3/2 to 20. Fractions for n take into consideration that uneven numbers of siloxyl groups may be present in the cycle.

Advantageously, cyclomethicone (e.g. decamethylcyclopentasiloxane) is used as the silicone oil to be used according to the invention. However, other silicone oils are also to be used advantageously for the purpose of the present invention, for example undecamethylcyclotrisiloxane, polydimethylsiloxane, poly(methylphenylsiloxane), cetyl-dimethicone, behenoxydimethicone.

Also advantageous are mixtures of cyclomethicone and isotridecyl isononanoate, and those of cyclomethicone and 2-ethylhexyl isostearate.

It is, however, also advantageous to choose silicone oils of similar constitution to the above-described compounds whose organic side chains are derivatized, for example polyethoxylated and/or polypropoxylated. These include, for example, polysiloxane-polyalkyl-polyether copolymers, such as cetyl-dimethicone copolyol, (cetyl-dimethicone copolyol (and) polyglyceryl-4-isostearate (and) hexyl laurate).

Also particularly advantageous are mixtures of cyclomethicone and isotridecyl isononanoate, and of cyclomethicone and 2-ethylhexyl isostearate.

The aqueous phase of the preparations according to the invention optionally advantageously comprises alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low carbon number, e.g. ethanol, isopropanol, 1,2-propanediol, glycerol, and, in particular, one or more thickeners which can advantageously be chosen from the group consisting of silicon dioxide and aluminum silicates.

Preparations according to the invention in the form of emulsions advantageously comprise, in particular, one or more hydrocolloids. These hydrocolloids can advantageously be chosen from the group of gums, polysaccharides, cellulose derivatives, phyllosilicates, polyacrylates and/or other polymers.

The gums include saps from plants or trees which harden in the air and form resins, or extracts from aquatic plants. From this group, for the purposes of the present invention, gum arabic, carob flour, tragacanth, karaya, guar gum, pectin, gellan gum, carrageen, agar, algins, chondrus, xanthan gum, for example, can be chosen advantageously.

Also advantageous is the use of derivatized gums, such as, for example, hydroxypropyl guar (Jaguar® HP 8).

The polysaccharides and polysaccharide derivatives include, for example, hyaluronic acid, chitin and chitosan, chondroitin sulfates, starch and starch derivatives.

The cellulose derivatives include, for example, methylcellulose, carboxymethylcellulose, hydroxyethylcellulose, hydroxypropylmethylcellulose.

The phyllosilicates include naturally occurring and synthetic clay earths, such as, for example, montmorillonite, bentonite, hectorite, laponite, magnesium aluminum silicates such as Veegum®. These can be used as such or in modified form, such as, for example, stearylalkonium hectorite.

In addition, silica gels can also be used advantageously.

The polyacrylates include, for example, Carbopol grades from Goodrich (Carbopol 980, 981, 1382, 5984, 2984, EDT 2001 or Pemulen TR2).

The polymers include, for example, polyacrylamides (Seppigel 305), polyvinyl alcohols, PVP, PVP/VA copolymers, polyglycols.

Preparation according to the invention in the form of emulsions comprise one or more emulsifiers. These emulsifiers can advantageously be chosen from the group of nonionic, anionic, cationic or amphoteric emulsifiers.

The nonionic emulsifiers include
a) partial fatty acid esters and fatty acid esters of polyhydric alcohols and ethoxylated derivatives thereof (e.g. glyceryl monostearates, sorbitan stearates, glyceryl stearyl citrates, sucrose stearates)
b) ethoxylated fatty alcohols and fatty acids
c) ethoxylated fatty amines, fatty acid amides, fatty acid alkanolamides
d) alkylphenol polyglycol ethers (e.g. Triton X).

The anionic emulsifiers include
a) soaps (e.g. sodium stearate)
b) fatty alcohol sulfates
c) mono-, di- and trialkyl phosphoric esters and ethoxylates thereof.

The cationic emulsifiers include
a) quaternary ammonium compounds with a long-chain aliphatic radical, e.g. distearyldimonium chloride.

The amphoteric emulsifiers include
a) alkylaminoalkanecarboxylic acids
b) betaines, sulfobetaines
c) imidazoline derivatives.

In addition, there are naturally occurring emulsifiers, which include beeswax, wool wax, lecithin and sterols.

O/W emulsifiers can be advantageously chosen, for example, from the group of polyethoxylated or polypropoxylated or polyethoxylated and polypropoxylated products, e.g.:

fatty alcohol ethoxylates, ethoxylated wool wax alcohols, polyethylene glycol ethers of the general formula R—O—(—CH$_2$—CH$_2$—O—)$_n$—R', fatty acid ethoxylates of the general formula R—COO—(—CH$_2$—CH$_2$—O—)$_n$—H, etherified fatty acid ethoxylates of the general formula R—COO—(—CH$_2$—CH$_2$—O—)$_n$—R', esterified fatty acid ethoxylates of the general formula R—COO—(—CH$_2$—CH$_2$—O—)$_n$—C(O)—R', polyethylene glycol glycerol fatty acid esters, ethoxylated sorbitan esters, cholesterol ethoxylates, ethoxylated triglycerides, alkyl ether carboxylic acids of the general formula R—O—(—CH$_2$—CH$_2$—O—)$_n$—CH$_2$—COOH and n is a number from 5 to 30, polyoxyethylene sorbitol fatty acid esters, alkyl ether sulfates of the general formula R—O—(—CH$_2$—CH$_2$—O—)$_n$—SO$_3$—H, fatty alcohol propoxylates of the general formula R—O—(—CH$_2$—CH(CH$_3$)—O—)$_n$—H, polypropylene glycol ethers of the general formula R—O—(—CH$_2$—CH(CH$_3$)—O—)$_n$—R', propoxylated wool wax alcohols, etherified fatty acid propoxylates R—COO—(—CH$_2$—CH(CH$_3$)—O—)$_n$—R', esterified fatty acid propoxylates of the general formula R—COO—(—CH$_2$—CH(CH$_3$)—O—)$_n$—C(O)—R', fatty acid propoxylates of the general formula R—COO—(—CH$_2$—CH(CH$_3$)—O—)$_n$—H, polypropylene glycol glycerol fatty acid esters, propoxylated sorbitan esters, cholesterol propoxylates, propoxylated triglycerides, alkyl ether carboxylic acids of the general formula R—O—(—CH$_2$—CH(CH$_3$)O—)$_n$—CH$_2$—COOH, alkyl ether sulfates or the parent acids of these sulfates of the general formula R—O—(—CH$_2$—CH(CH$_3$)—O—)$_n$—SO$_3$—H, fatty alcohol ethoxylates/propoxylates of the general formula R—O—X$_n$—Y$_m$—H, polypropylene glycol ethers of the general formula R—O—X$_n$—Y$_m$—R', etherified fatty acid propoxylates of the general formula R—COO—X$_n$—Y$_m$—R', fatty acid ethoxylates/propoxylates of the general formula R—COO—X$_n$—Y$_m$—H.

According to the invention, particularly advantageous polyethoxylated or polypropoxylated or polyethoxylated and polypropoxylated O/W emulsifiers used are those chosen from the group of substances having HLB values, of 11–18, very particularly preferably having HLB values of 14.5–15.5, provided the O/W emulsifiers have saturated radicals R and R'. If the O/W emulsifiers have unsaturated radicals R and/or R', or isoalkyl derivatives are present, then the preferred HLB value of such emulsifiers can also be lower or higher.

It is advantageous to choose the fatty alcohol ethoxylates from the group of ethoxylated stearyl alcohols, cetyl alcohols, cetylstearyl alcohols (cetearyl alcohols). Particular preference is given to:

polyethylene glycol(13) stearyl ether (steareth-13), polyethylene glycol(14) stearyl ether (steareth-14), polyethylene glycol(15) stearyl ether (steareth-15), polyethylene glycol (16) stearyl ether (steareth-16), polyethylene glycol(17) stearyl ether (steareth-17), polyethylene glycol(18) stearyl ether (steareth-18), polyethylene glycol(19) stearyl ether (steareth-19), polyethylene glycol(20) stearyl ether (steareth-20), polyethylene glycol(12) isostearyl ether (isosteareth-12), polyethylene glycol(13) isostearyl ether (isosteareth-13), polyethylene glycol(14) isostearyl ether (isosteareth-14), polyethylene glycol(15) isostearyl ether (isosteareth-15), polyethylene glycol(16) isostearyl ether (isosteareth-16), polyethylene glycol(17) isostearyl ether (isosteareth-17), polyethylene glycol(18) isostearyl ether (isosteareth-18), polyethylene glycol(19) isostearyl ether (isosteareth-19), polyethylene glycol(20) isostearyl ether (isosteareth-20), polyethylene glycol(13) cetyl ether (ceteth-13), polyethylene glycol(14) cetyl ether (ceteth-14), polyethylene glycol (15) cetyl ether (ceteth-15), polyethylene glycol(16) cetyl ether (ceteth-16), polyethylene glycol(17) cetyl ether (ceteth-17), polyethylene glycol(18) cetyl ether (ceteth-18), polyethylene glycol(19) cetyl ether (ceteth-19), polyethylene glycol(20) cetyl ether (ceteth-20), polyethylene glycol(13) isocetyl ether (isoceteth-13), polyethylene glycol(14) isocetyl ether (isoceteth-14), polyethylene glycol(15) isocetyl ether (isoceteth-15), polyethylene glycol(16) isocetyl ether (isoceteth-16), polyethylene glycol(17) isocetyl ether (isoceteth-17), polyethylene glycol(18) isocetyl ether (isoceteth-18), polyethylene glycol(19) isocetyl ether (isoceteth-19), polyethylene glycol(20) isocetyl ether (isoceteth-20), polyethylene glycol(12) oleyl ether (oleth-12), polyethylene glycol(13) oleyl ether (oleth-13), polyethylene glycol(14) oleyl ether (oleth-14), polyethylene glycol(15) oleyl ether (oleth-15), polyethylene glycol(12) lauryl ether (laureth-12), polyethylene glycol(12) isolauryl ether (isolaureth-12), polyethylene glycol(13) cetylstearyl ether (ceteareth-13), polyethylene glycol(14) cetylstearyl ether (ceteareth-14), polyethylene glycol(15) cetylstearyl ether (ceteareth-15), polyethylene glycol(16) cetylstearyl ether (ceteareth-16), polyethylene glycol(17) cetylstearyl ether (ceteareth-17), polyethylene glycol(18) cetylstearyl ether (ceteareth-18), polyethylene glycol (19) cetylstearyl ether (ceteareth-19), polyethylene glycol(20) cetylstearyl ether (ceteareth-20).

It is also advantageous to choose the fatty acid ethoxylates from the following group:

polyethylene glycol(20) stearate, polyethylene glycol(21) stearate, polyethylene glycol(22) stearate, polyethylene glycol(23) stearate, polyethylene glycol(24) stearate, polyethylene glycol(25) stearate, polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol(21) isostearate, polyethylene glycol(22) isostearate, polyethylene glycol(23) isostea rate, polyethylene glycol(24) isostea rate, polyethylene glycol(25) isostearate, polyethylene glycol(12) oleate, polyethylene glycol(13) oleate, polyethylene glycol(14) oleate, polyethylene glycol(15) oleate, polyethylene glycol(16) oleate, polyethylene glycol(17) oleate, polyethylene glycol(18) oleate, polyethylene glycol(19) oleate, polyethylene glycol(20) oleate.

The ethoxylated alkyl ether carboxylic acid or salt thereof which can be used is advantageously sodium laureth-11 carboxylate.

Sodium laureth-14 sulfate can be used advantageously as alkyl ether sulfate.

An advantageous ethoxylated cholesterol derivative which can be used is polyethylene glycol(30) cholesteryl ether. Polyethylene glycol(25) soyasterol has also proven successful.

Ethoxylated triglycerides which can be advantageously used are polyethylene glycol(60) Evening Primrose glycerides.

It is also advantageous to choose the polyethylene glycol glycerol fatty acid esters from the group polyethylene glycol (20) glyceryl laurate, polyethylene glycol(21) glyceryl laurate, polyethylene glycol(22) glyceryl laurate, polyethylene glycol(23) glyceryl laurate, polyethylene glycol(6) glyceryl caprate, polyethylene glycol(20) glyceryl oleate, polyethylene glycol(20) glyceryl isostearate, polyethylene glycol (18) glyceryl oleate/cocoate.

It is likewise favorable to choose the sorbitan esters from the group polyethylene glycol(20) sorbitan monolaurate, polyethylene glycol(20) sorbitan monostearate, polyethylene glycol(20) sorbitan monoisostearate, polyethylene glycol(20) sorbitan monopalmitate, polyethylene glycol(20) sorbitan monooleate.

Advantageous W/O emulsifiers which can be used are: fatty alcohols having 8 to 30 carbon atoms, monoglycerol esters of saturated and/or unsaturated, branched and/or unbranched alkanecarboxylic acids having a chain length of from 8 to 24, in particular 12–18, carbon atoms, diglycerol esters of saturated and/or unsaturated, branched and/or unbranched alkanecarboxylic acids having a chain length of from 8 to 24, in particular 12–18, carbon atoms, monoglycerol ethers of saturated and/or unsaturated, branched and/or unbranched alcohols having a chain length of from 8 to 24, in particular 12–18, carbon atoms, diglycerol ethers of saturated and/or unsaturated, branched and/or unbranched alcohols having a chain length of from 8 to 24, in particular 12–18, carbon atoms, propylene glycol esters of saturated and/or unsaturated, branched and/or unbranched alkanecarboxylic acids having a chain length of from 8 to 24, in particular 12–18, carbon atoms, and sorbitan esters of saturated and/or unsaturated, branched and/or unbranched alkanecarboxylic acids having a chain length of from 8 to 24, in particular 12–18, carbon atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol(2) stearyl ether (steareth-2), glyceryl monolaurate, glyceryl monocaprate, glyceryl monocaprylate.

The gel creams according to the invention can comprise dyes and/or color pigments. The dyes and color pigments can be chosen from the corresponding positive list of the Cosmetics Directive or the EC list of cosmetic colorants. In most cases they are identical to the dyes approved for foods. Advantageous color pigments are, for example, titanium dioxide, mica, iron oxides (e.g. $Fe_2O_3$, $Fe_3O_4$, FeO(OH)) and/or tin oxide. Advantageous dyes are, for example, carmine, Berlin blue, chrome oxide green, ultramarine blue and/or manganese violet. It is particularly advantageous to choose the dyes and/or color pigments from the following list. The Colour Index Numbers (CIN) are taken from the *Rowe Colour Index*, 3rd Edition, Society of Dyers and Colourists, Bradford, England, 1971.

| Chemical or other name | CIN | Color |
|---|---|---|
| Pigment Green | 10006 | green |
| Acid Green 1 | 10020 | green |
| 2,4-Dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxynaphthalene | 12085 | red |
| Pigment Red 3 | 12120 | red |
| Ceres red; Sudan red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'-sulfodiethylamido-1'-phenylazo)-3-hydroxy-5"-chloro-2",4"-dimethoxy-2-naphthanilide | 12490 | red |
| Disperse Yellow 16 | 12700 | yellow |
| 1-(4-Sulfo-1-phenylazo)-4-aminobenzene-5-sulfonic acid | 13015 | yellow |
| 2,4-Dihydroxyazobenzene-4'-sulfonic acid | 14270 | orange |
| 2-(2,4-Dimethylphenylazo-5-sulfo)-1-hydorxynaphthalene-4-sulfonic acid | 14700 | red |
| 2-(4-Sulfo-1-naphthylazo)-1-naphthol-4-sulfonic acid | 14720 | red |
| 2-(6-Sulfo-2,4-xylylazo)-1-naphthol-5-sulfonic acid | 14815 | red |
| 1-(4'-Sulfophenylazo)-2-hydroxynaphthalene | 15510 | orange |
| 1-(2-Sulfo-4-chloro-5-carboxy-1-phenylazo)-2-hydroxynaphthalene | 15525 | red |
| 1-(3-Methylphenylazo-4-sulfo)-2-hydroxynaphthalene | 15580 | red |
| 1-(4',(8')-Sulfonaphthylazo)-2-hydroxynaphthalene | 15620 | red |
| 2-Hydroxy-1,2'-azonaphthalene-1'-sulfonic acid | 15630 | red |
| 3-Hydroxy-4-phenylazo-2-naphthylcarboxylic acid | 15800 | red |
| 1-(2-Sulfo-4-methyl-1-phenylazo)-2-naphthylcarboxylic acid | 15850 | red |
| 1-(2-Sulfo-4-methyl-5-chloro-1-phenylazo)-2-hydroxynaphthalene-3-carboxylic acid | 15865 | red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | orange |
| 1-(4-Sulfo-1-phenylazo)-2-naphthol-6-sulfonic acid | 15985 | yellow |
| Allura Red | 16035 | red |
| 1-(4-Sulfo-1-naphthylazo)-2-naphthol-3,6-disulfonic acid | 16185 | red |
| Acid Orange 10 | 16230 | orange |
| 1-(4-Sulfo-1-naphthylazo)-2-naphthol-6,8-disulfonic acid | 16255 | red |
| 1-(4-Sulfo-1-naphthylazo)-2-naphthol-3,6,8-trisulfonic acid | 16290 | red |
| 8-Amino-2-phenylazo-1-naphthol-3,6-disulfonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulfo-1-phenylazo)-1-(4-sulfophenyl)-5-hydroxy-pyrazolone-3-carboxylic acid | 19140 | yellow |
| Pigment Yellow 16 | 20040 | yellow |
| 2,6-(4'-Sulfo-2",4"-dimethyl)bisphenylazo)-1,3-dihydroxybenzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4"-Sulfo-1"-phenylazo)-7'-sulfo-1'-naphthylazo]-1-hydroxy-7-aminonaphthalene-3,6-disulfonic acid | 27755 | black |
| 4'-[(4"-Sulfo-1"-phenylazo)-7'-sulfo-1'-naphthylazo]-1-hydroxy-8-acetylaminonaphthalene-3,5-disulfonic acid | 28440 | black |
| Direct Orange 34, 39, 44, 46, 60 | 40215 | orange |
| Food Yellow | 40800 | orange |
| trans-β-Apo-8'-carotinaldehyde ($C_{30}$) | 40820 | orange |
| trans-Apo-8'-carotinic acid ($C_{30}$)-ethyl ester | 40825 | orange |
| Canthaxanthin | 40850 | orange |
| Acid Blue 1 | 42045 | blue |
| 2,4-Disulfo-5-hydroxy-4'-4"-bis(diethylamino)-triphenylcarbinol | 42051 | blue |
| 4-[(4-N-Ethyl-p-sulfobenzylamino)phenyl(4-hydroxy-2-sulfophenyl)(methylene)-1-(N-ethyl-N-p-sulfobenzyl)-2,5-cyclohexadienimine] | 42053 | green |
| Acid Blue 7 | 42080 | blue |
| (N-Ethyl-p-sulfobenzylamino)phenyl(2-sulfophenyl)-methylene-(N-ethyl-N-p-sulfobenzyl)$\Delta^{2,5}$-cyclohexadienimine | 42090 | blue |
| Acid Green 9 | 42100 | green |
| Diethyldisulfobenzyldi-4-amino-2-chlorodi-2-methyl-fuchsonimmonium | 42170 | green |
| Basic Violet 14 | 42510 | violet |
| Basic Violet 2 | 42520 | violet |
| 2'-Methyl-4'-(N-ethyl-N-m-sulfobenzyl)amino-4"-(N-diethyl)amino-2-methyl-N-ethyl-N-m-sulfobenzylfuchsonimmonium | 42735 | blue |
| 4'-(N-Dimethyl)amino-4"-(N-phenyl)-aminonaphtho-N-dimethyl-fuchsonimmonium | 44045 | blue |
| 2-Hydroxy-3,6-disulfo-4,4'-bisdimethylaminonaphtho-fuchsonimmonium | 44090 | green |
| Acid Red 52 | 45100 | red |
| 3-(2'-Methylphenylamino)-6-(2'-methyl-4'-sulfophenylamino)-9-(2"-carboxyphenyl)-xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulfonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium-aluminum complex | 55000 | red |
| 3-Oxypyrene-5,8,10-sulfonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulfo-p-toluidino)anthraquinone | 61570 | green |
| Acid Blue 80 | 61585 | blue |
| Acid Blue 62 | 62045 | blue |

-continued

| Chemical or other name | CIN | Color |
|---|---|---|
| N,N'-Dihydro-1,2,1',2'-anthraquinone azine | 69800 | blue |
| Vat Blue 6; Pigment Blue 64 | 69825 | blue |
| Vat Orange 7 | 71105 | orange |
| Indigo | 73000 | blue |
| Indigo-disulfonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated phthalocyanine | 74260 | green |
| Natural Yellow 6,19; Natural Red 1 | 75100 | yellow |
| Bixin, Norbixin | 75120 | orange |
| Lycopene | 75125 | yellow |
| trans-alpha-, beta- and gamma-carotene | 75130 | orange |
| Keto-and/or hydroxyl derivates of carotene | 75135 | yellow |
| Guanine or pearlescent agent | 75170 | white |
| 1,7-Bis(4-hydroxy-3-methoxyphenyl)-1,6-heptadiene-3,5-dione | 75300 | yellow |
| Complex salt (Na, Al, Ca) of carminic acid | 75470 | red |
| Chlorophyll a and b; copper compounds of chlorophylls and chlorophyllins | 75810 | green |
| Aluminum | 77000 | white |
| Hydrated alumina | 77002 | white |
| Hydrous aluminum silicates | 77004 | white |
| Ultramarine | 77007 | blue |
| Pigment Red 101 and 102 | 77015 | red |
| Barium sulfate | 77120 | white |
| Bismuth oxychloride and its mixtures with mica | 77163 | white |
| Calcium carbonate | 77220 | white |
| Calcium sulfate | 77231 | white |
| Carbon | 77266 | black |
| Pigment black 9 | 77267 | black |
| Carbo medicinalis vegetabilis | 77268:1 | black |
| Chromium oxide | 77288 | green |
| Chromium oxide, hydrous | 77289 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxide | 77491 | red |
| Hydrated iron oxide | 77492 | yellow |
| Iron oxide | 77499 | black |
| Mixtures of iron(II)- and iron(III)hexacyanoferrate | 77510 | blue |
| Pigment White 18 | 77713 | white |
| Manganese ammonium diphosphate | 77742 | violet |
| Manganese phosphate; $Mn_3(PO_4)_2 \cdot 7\ H_2O$ | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)isoalloxazine, lactoflavine | | yellow |
| Sugar coloring | | brown |
| Capsanthin, capsorubin | | orange |
| Betanin | | red |
| Benzopyrylium salts, anthocyans | | red |
| Aluminum, zinc, magnesium and calcium stearate | | white |
| Bromothymol blue | | blue |
| Bromocresol green | | green |
| Acid Red 195 | | red |

It may also be favorable to choose as dye one or more substances from the following group: 2,4-dihydroxyazobenzene, 1-(2'-chloro-4'-nitro-1'-phenylazo)-2-hydroxy-naphthalene, Ceres Red, 2-(4-sulfo-1-naphthylazo)-1-naphthol4-sulfonic acid, calcium salt of 2-hydroxy-1,2'-azonaphthalene-1'-sulfonic acid, calcium and barium salts of 1-(2-sulfo-4-methyl-1-phenylazo)-2-naphthylcarboxylic acid, calcium salt of 1-(2-sulfo-1-naphthylazo)-2-hydroxynaphthalene-3-carboxylic acid, aluminum salt of 1-(4-sulfo-1-phenylazo)-2-naphthol-6-sulfonic acid, aluminum salt of 1-(4-sulfo-1-naphthylazo)-2-naphthol-3,6-disulfonic acid, 1-(4-sulfo-1-naphthylazo)-2-naphthol-6,8-disulfonic acid, aluminum salt of 4-(4-sulfo-1-phenylazo)-1-(4-sulfophenyl)-5-hydroxypyrazolone-3-carboxylic acid, aluminum and zirconium salts of 4,5-dibromofluorescein, aluminum and zirconium salts of 2,4,5,7-tetrabromofluorescein, 3',4',5',6'-tetrachloro -2,4,5,7-tetrabromofluorescein and its aluminum salt, aluminum salt of 2,4,5,7-tetraiodofluorescein, aluminum salt of quinophthalone disulfonic acid, aluminum salt of indigo disulfonic acid, red and black iron oxide (CIN: 77 491 (red) and 77 499 (black)), iron oxide hydrate (CIN: 77 492), manganese ammonium diphosphate and titanium dioxide.

Also advantageous are oil-soluble natural dyes, such as, for example, paprika extracts, β-carotene or cochenille.

Also advantageous for the purposes of the present invention are gel creams with a content of pearlescent pigments. Preference is given in particular to the types of pearlescent pigments listed below:

1. Natural pearlescent pigments, such as, for example "pearl essence" (guanine/hypoxanthin mixed crystals from fish scales) and "mother of pearl" (ground mussel shells)
2. Monocrystalline pearlescent pigments, such as, for example, bismuth oxychloride (BiOCl)
3. Layer-substrate pigments: e.g. mica/metal oxide.

Bases for pearlescent pigments are, for example, pulverulent pigments or castor oil dispersions of bismuth oxychloride and/or titanium dioxide, and bismuth oxychloride and/or titanium dioxide on mica. The luster pigment listed under CIN 77163, for example, is particularly advantageous.

Also advantageous are, for example, the following types of pearlescent pigment based on mica/metal oxide:

| Group | Coating/layer thickness | Color |
|---|---|---|
| Silver-white pearlescent pigments | $TiO_2$: 40–60 μm | Silver |
| Interference pigments | $TiO_2$: 40–60 μm | Yellow |
| | $TiO_2$: 40–60 μm | Red |
| | $TiO_2$: 40–60 μm | Blue |
| | $TiO_2$: 40–60 μm | Green |
| Color luster pigments | $Fe_2O_3$ | Bronze |
| | $Fe_2O_3$ | Copper |
| | $Fe_2O_3$ | Red |
| | $Fe_2O_3$ | Red-violet |
| | $Fe_2O_3$ | Red-green |
| | $Fe_2O_3$ | Black |
| Combination pigments | $TiO_2/Fe_2O_3$ | Gold shades |
| | $TiO_2/Cr_2O_3$ | Green |
| | $TiO_2$/Berlin blue | Deep blue |
| | $TiO_2$/carmine | Red |

Particular preference is given, for example, to the pearlescent pigments obtainable from Merck under the trade names Timiron, Colorona or Dichrona.

The list of given pearlescent pigments is not of course intended to be limiting. Pearlescent pigments which are advantageous for the purposes of the present invention are obtainable by numerous methods known per se. For example, other substrates apart from mica can be coated with further metal oxides, such as, for example, silica and the like $SiO_2$ particles coated with, for example, $TiO_2$ and $Fe_2O_3$ ("ronaspheres"), which are marketed by Merck and are particularly suitable for the optical reduction of fine lines, are advantageous.

It can moreover be advantageous to dispense completely with a substrate such as mica. Particular preference is given to iron pearlescent pigments prepared without the use of mica. Such pigments are obtainable, for example, under the trade name Sicopearl Kupfer 1000 from BASF.

In addition, also particularly advantageous are effect pigments which are obtainable under the trade name Metasome Standard/Glitter in various colors (yellow, red, green, blue) from Flora Tech. The glitter particles are present here in mixtures with various auxiliaries and dyes (such as, for example, the dyes with the Colour Index (CI) Numbers 19140, 77007, 77289, 77491).

The dyes and pigments may be present either individually or in a mixture, and can be mutually coated with one another, different coating thicknesses generally giving rise to different color effects. The total amount of dyes and color-imparting pigments is advantageously chosen from the range from e.g. 0.1% by weight to 30% by weight, preferably from 0.5 to 15% by weight, in particular from 1.0 to 10% by weight, in each case based on the total weight of the preparations.

The gel creams according to the invention can, in particular, advantageously be used as eyeshadows.

Particularly advantageous preparations are also obtained when antioxidants are used as additives or active ingredients. According to the invention, the preparations advantageously comprise one or more antioxidants. Antioxidants which are favorable but which are nevertheless optional may be all antioxidants which are customary or suitable for cosmetic and/or dermatological applications.

It is also advantageous to add antioxidants to the preparations according to the invention. The antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothio-glucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulphoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide), and the derivatives (salts, esters, ethers, sugars, nucleotides, nucleosides, peptides and lipids) of said active ingredients which are suitable according to the invention.

For the purposes of the present invention, oil-soluble antioxidants can be used particularly advantageously.

A surprising property of the present invention is that preparations according to the invention are very good vehicles for cosmetic or dermatological active ingredients into the skin, preferred active ingredients being antioxidants which are able to protect the skin against oxidative stress. Preferred antioxidants are vitamin E and derivatives thereof and vitamin A and derivatives thereof.

The amount of antioxidants (one or more compounds) in the preparations is preferably from 0.001 to 30% by weight, particularly preferably 0.05–20% by weight, in particular 1–10% by weight, based on the total weight of the preparation.

If vitamin E and/or derivatives thereof are the antioxidant or antioxidants, the respective concentrations thereof are advantageously chosen from the range 0.001–10% by weight, based on the total weight of the formulation.

If vitamin A or vitamin A derivatives or carotenes or derivatives thereof are used as the antioxidant or antioxidants, the respective concentrations thereof are advantageously chosen from the range 0.001–10% by weight, based on the total weight of the formulation.

The person skilled in the art is of course aware that cosmetic preparations are in most cases, inconceivable without the customary auxiliaries and additives. The cosmetic and dermatological preparations according to the invention can, accordingly, also comprise cosmetic auxiliaries, as are customarily used in such preparations, for example bodying agents, stabilizers, fillers, preservatives, perfumes, antifoams, dyes, pigments which have a coloring action, thickeners, surface-active substances, emulsifiers, emollients, moisturizers and/or humectants, anti-inflammatory substances, additional active ingredients such as vitamins or proteins, sunscreens, insect repellants, bactericides, virucides, water, salts, antimicrobial, proteolytic or keratolytic substances, medicaments or other customary constituents of a cosmetic or dermatological formulation such as alcohols, polyols, polymers, foam stabilizers, organic solvents or also electrolytes.

The latter can be chosen, for example, from the group of salts containing the following anions: chlorides, also inorganic oxo element anions, of these, in particular sulfates, carbonates, phosphates, borates and aluminates. Electrolytes based on organic anions are also advantageous, e.g. lactates, acetates, benzoates, propionates, tartrates, citrates, amino acids, ethylenediaminetetraacetic acid and salts thereof and others. Preferred cations of the salts are ammonium, alkylammonium, alkali metal, alkaline earth metal, magnesium, iron or zinc ions. It goes without saying that only physiologically acceptable electrolytes should be used in cosmetics. Particular preference is given to potassium chloride, sodium chloride, magnesium sulfate, zinc sulfate and mixtures thereof.

Corresponding requirements apply mutatis mutandis to the formulation of medicinal preparations.

The gel creams according to the invention can be used as a base for cosmetic or dermatological formulations. The latter can have the customary composition and be used, for example, for the treatment and care of the skin and/or the hair, as lip care product, as deodorant product and as make-up or make-up remover product in decorative cosmetics or as a sunscreen preparation. For use, the cosmetic and dermatological preparations according to the invention are applied to the skin and/or the hair in a sufficient amount in a manner customary for cosmetics or dermatological compositions.

For the purposes of the present invention, cosmetic or topical dermatological compositions can accordingly, depending on their composition, be used, for example, as a skin protection cream, cleansing milk, sunscreen lotion, nutrient cream, day or night cream, etc. In some circumstances it is possible and advantageous to use the compositions according to the invention as a base for pharmaceutical formulations.

The cosmetic or dermatological compositions according to the invention can, for example, be in the form of preparations which can be sprayed from aerosol containers, squeezable bottles or by means of a pump device, or in the form of a liquid composition which can be applied by means of roll-on devices, but also in the form of an emulsion which can be applied from normal bottles and containers.

Suitable propellants for cosmetic or dermatological preparations which can be sprayed from aerosol containers for the purposes of the present invention are the customary known readily volatile, liquefied propellants, for example hydrocarbons (propane, butane, isobutane), which can be used alone or in a mixture with one another. Compressed air is also used advantageously.

The person skilled in the art is of course aware that there are propellants which are non-toxic per se which would be suitable in principle for realizing the present invention in the form of aerosol preparations, but which must nevertheless be avoided because of their unacceptable impact on the environment or other accompanying circumstances, in particular fluorocarbons and chlorofluorocarbons (CFCs).

Those cosmetic and dermatological preparations which are in the form of a sunscreen are also favorable. As well as the active ingredient combinations according to the invention, these preferably additionally comprise at least one UV-A filter substance and/or at least one UV-B filter substance and/or at least one inorganic pigment.

For the purposes of the present invention, however, it is also advantageous to provide those cosmetic and dermatological preparations whose main purpose is not protection against sunlight, but which nevertheless have a content of UV protectants. Thus, for example, UV-A or UV-B filter substances are usually incorporated into day creams.

UV protectants, like antioxidants and, if desired, preservatives, also effectively protect the preparations themselves against decay.

Furthermore, preparations according to the invention can advantageously comprise substances which absorb UV radiation in the UV-B range, the total amount of filter substances being, for example, from 0.1% by weight to 30% by weight, preferably from 0.5 to 10% by weight, in particular from 1.0 to 6.0% by weight, based on the total weight of the preparations, in order to provide cosmetic preparations which protect the hair and/or the skin from the whole region of ultraviolet radiation. They can also be used as sunscreens for the hair or the skin.

If the emulsions according to the invention comprise UV-B filter substances, the latter may be oil-soluble or water-soluble. Examples of oil-soluble UV-B filters which are advantageous according to the invention are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethyl-amino)benzoate, amyl 4-(dimethylamino) benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy4-methoxybenzophenone, 2-hydroxy-4-methoxy4'-methylbenzophenone, 2,2'-dihydroxy-4-methoxybenzophenone;

esters of benzalmalonic acid, preferably di(2-ethylhexyl) 4-methoxybenzalmalonate;

derivatives of 1,3,5-triazine, preferably 2,4,6-trianilino(p-carbo-2'-ethyl-1'-hexyloxy)-1,3,5-triazine.

The list of said UV-B filters, which may be used in combination with the active ingredient combinations according to the invention, is of course not intended to be limiting.

It can also be advantageous to formulate lipodispersions according to the invention with UV-A filters which have hitherto been customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione.

Cosmetic and dermatological preparations according to the invention can also comprise inorganic pigments which are customarily used in cosmetics for protecting the skin against UV rays. These are oxides of titanium, zinc, iron, zirconium, silicon, manganese, aluminum, cerium and mixtures thereof, and modifications in which the oxides are the active agents. Particular preference is given to pigments based on titanium dioxide.

Further constituents which can be used are:

fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;

alcohols, diols or polyols of low carbon number, and ethers thereof, preferably ethanol, isopropanol, propylene glycol, glycerol, ethylene glycol, ethylene glycol monoethyl or monobutyl ethers, propylene glycol monomethyl, monoethyl or monobutyl ethers, diethylene glycol monomethyl or monoethyl ethers and analogous products.

The examples below serve to illustrate the present invention without limiting it. The numerical values in the examples refer to percentages by weight, based on the total weight of the respective preparations.

EXAMPLE 1

(Hydrodispersion Gel)

|  | % by wt |
|---|---|
| PEG-8 (polyethylene glycol 400) | 5.00 |
| Ethanol | 10.00 |
| Aristoflex AVC | 0.70 |
| Triglyceride, liquid | 1.50 |
| Glycerol | 5.00 |
| Panthenol | 0.50 |
| Tocopherol acetate | 0.50 |
| Perfume, preservatives, NaOH, dyes, antioxidants etc. | q.s. |
| Water | ad 100.00 |

EXAMPLE 2

(Hydrodispersion Gel)

|  | % by wt. |
|---|---|
| Xanthan gum | 0.20 |
| Aristoflex AVC | 1.00 |
| Glycerol | 5.00 |
| 1,3-Butylene glycol | 2.00 |
| Dimethicone | 3.00 |
| Isopropyl palmitate | 1.50 |
| Perfume, preservatives, NaOH, dyes, antioxidants, pigments etc. | q.s. |
| Water | ad 100.00 |

EXAMPLE 3

|  | % by wt. |
|---|---|
| Sucrose stearate | 1.00 |
| Cetearyl alcohol | 0.50 |
| PEG-5 soyasterol | 2.00 |
| Tocopherol | 1.00 |
| Aristoflex AVC | 1.00 |
| Glycerol | 3.00 |
| EDTA | 0.50 |
| Antioxidants, preservatives, neutralizing agents, perfume, dyes, pigments | q.s. |
| Water | ad 100.00 |

EXAMPLE 4

|  | % by wt. |
|---|---|
| Glycerol monostearate | 2.00 |
| PEG-40 glyceryl stearate | 0.50 |
| Aristoflex AVC | 1.00 |
| Magnesium aluminum silicate | 0.30 |
| Glycerol | 5.00 |
| 1,3-Butylene glycol | 2.00 |
| Panthenol | 2.50 |
| Perfume, preservatives, NaOH, complexing agent, dyes, antioxidants, pigments etc. | q.s. |
| Water | ad 100.00 |

EXAMPLE 5

|  | % by wt. |
|---|---|
| Glyceryl stearate citrate | 1.50 |
| Cetyl alcohol | 0.50 |
| Jojoba oil | 2.00 |
| Aristoflex AVC | 0.50 |
| Chitosan | 0.50 |
| Lactic acid (90% strength) | 0.30 |
| Glycerol | 5.00 |
| Perfume, preservatives, NaOH, dyes, antioxidants, pigments etc. | q.s. |
| Water | ad 100.00 |

EXAMPLE 6

|  | % by wt |
|---|---|
| Polyglyceryl-3 methylglucose distearate | 2.00 |
| Sorbitan stearate | 0.50 |
| Glycerol | 3.00 |
| $C_{12-15}$-Alkyl benzoates | 5.00 |
| Caprylic/capric triglycerides | 3.00 |
| Aristoflex AVC | 0.50 |
| Perfume, preservatives, NaOH, dyes, antioxidants, pigments etc. | q.s. |
| Water | ad 100.00 |

EXAMPLE 7

|  | % by wt |
|---|---|
| Decyl glucoside | 1.00 |
| Glyceryl lanolate | 1.50 |
| Dimethicone copolyol | 2.00 |
| Triceteareth-4 phosphate | 0.70 |
| Panthenol | 1.50 |
| Isopropyl palmitate | 1.00 |
| Aristoflex AVC | 1.00 |
| Perfume, preservatives, NaOH, dyes, antioxidants, pigments etc. | q.s. |
| Water | ad 100.00 |

EXAMPLE 8

|  | % by wt |
|---|---|
| Stearyl alcohol | 2.00 |
| Caprylic/capric triglycerides | 2.00 |
| Paraffin oil | 2.00 |
| Octyldodecanol | 3.00 |
| Glycerol | 3.00 |
| Acrylates/$C_{10-30}$-alkyl acrylate cross polymer | 0.15 |
| Aristoflex AVC | 0.20 |
| Tocopheryl acetate | 0.50 |
| Perfume, preservatives, NaOH, dyes, antioxidants, pigments etc. | q.s. |
| Water, demineralized | ad 100.00 |

What is claimed is:

1. A cosmetic or dermatological gel cream of the oil-in-water type, comprising (i) up to 90% by weight of a water phase, (ii) up to 20% by weight of a lipid phase, based on the total weight of the preparation, (iii) up to 5% by weight of one or more emulsifiers, (iv) also comprising up to 5% by weight of one or more ammonium acryloyldimethyltaurates/vinylpyrrolidone copolymers.

2. The gel cream as claimed in claim 1, wherein its lipid content ranges from 0.5% by weight to 20% by weight.

3. The gel cream of claim 2, wherein said lipid content ranges form 5–10% by weight.

4. The gel cream as claimed in claim 3, wherein its lipid content is up to 7.5% by weight.

5. The gel cream as claimed in claim 1, further comprising one or more dyes, coloring pigments or a combination thereof.

6. An eyeshadow comprising a gel cream of claim 5.

7. The gel cream as claimed in claim 5, wherein the total amount of the dyes and coloring pigments is from 0.1% by weight to 30% by weight based on the total weight of the preparations.

8. The gel cream of claim 7, wherein said amount is 0.5–15% by weight.

9. The gel cream of claim 7, wherein said amount is 1–10% by weight.

* * * * *

UNITED STATES PATENT AND TRADEMARK OFFICE
CERTIFICATE OF CORRECTION

PATENT NO. : 6,620,420 B2 Page 1 of 1
DATED : September 16, 2003
INVENTOR(S) : Lanzendorfer et al.

It is certified that error appears in the above-identified patent and that said Letters Patent is hereby corrected as shown below:

Column 18,
Line 65, "ranges form" should read -- ranges from --

Signed and Sealed this

Twenty-second Day of March, 2005

JON W. DUDAS
*Director of the United States Patent and Trademark Office*